United States Patent [19]

Woodruff et al.

[11] Patent Number: 4,939,376
[45] Date of Patent: Jul. 3, 1990

[54] LIGHT COLLECTION DEVICE FOR FLAME EMISSION DETECTORS

[75] Inventors: Stephen D. Woodruff; Ronald G. Logan; Richard L. Pineault, all of Morgantown, W. Va.

[73] Assignee: The United States of America as represented by the United States Department of Energy, Washington, D.C.

[21] Appl. No.: 337,979

[22] Filed: Apr. 14, 1989

[51] Int. Cl.⁵ .............................. G01J 1/00; G01J 3/30
[52] U.S. Cl. ..................................... 250/554; 250/228; 356/315; 356/236
[58] Field of Search ................. 250/228, 554; 356/315, 356/236

[56] References Cited

U.S. PATENT DOCUMENTS

| | | | |
|---|---|---|---|
| 3,137,759 | 6/1964 | Isreeli | 356/315 |
| 3,692,415 | 9/1972 | Shiller | 356/315 |
| 4,466,943 | 8/1984 | Murase et al. | 356/315 |
| 4,487,504 | 12/1984 | Goldsmith | 250/228 |
| 4,616,137 | 10/1986 | Goff et al. | 250/554 |
| 4,746,214 | 5/1988 | Akiyama et al. | 250/228 |

OTHER PUBLICATIONS

Chase et al., "New Scanner Uses Visible Light to Detect Flame", *Power Engineering*, 4/82, pp. 68–71.
Hensel et al., "On-Line, Real-Time Alkali Monitor for Process Stream Analysis", *Rev. Sci. Instrum.*, 58(9): 1647–1654 (1987).
Wolpert, "Unraveling the Mystery of Integrated Spheres", *Electro Optics*.

Primary Examiner—David C. Nelms
Assistant Examiner—Michael Messinger
Attorney, Agent, or Firm—Stephen D. Hamel; William R. Moser; Richard E. Constant

[57] ABSTRACT

A light collection device for use in a flame emission detection system such as an on-line, real-time alkali concentration process stream monitor is disclosed which comprises a sphere coated on its interior with a highly diffuse reflective paint which is positioned over a flame emission source, and one or more fiber optic cables which transfer the light generated at the interior of the sphere to a detecting device. The diffuse scattering of the light emitted by the flame uniformly distributes the light in the sphere, and the collection efficiency of the device is greater than that obtainable in the prior art. The device of the present invention thus provides enhanced sensitivity and reduces the noise associated with flame emission detectors, and can achieve substantial improvements in alkali detection levels.

4 Claims, 2 Drawing Sheets

LIGHT COLLECTION DEVICE FOR FLAME EMISSION DETECTORS

Field of the Invention the invention relates in general to a device for improving the sensitivity of a flame emission detection system, and in particular to a light collection device for a flame emission source which utilizes an internally coated integrating sphere.

Background of the Invention

There are many devices known which make use of a flame or burner in the detection of particular components of gases. Included in such devices are monitors of alkali concentrations in coal-derived gaseous process streams which operate by introducing a sample of a process stream to a high-temperature flame, which emits light at the characteristic wavelengths of elements such as sodium and potassium. The emitted light can then be transferred to a detection system where the levels of these elements are determined. Detection systems such as these are important in that the alkali content of coal-derived gaseous fuels and their combustion products can be used to assess their potential for causing corrosion and erosion of downstream components in hot environments, such as a gas turbine.

One device presently known for assessing process streams is the on-line, real-time alkali monitor disclosed in Hensel et al., *Rev. Sci. Instrum.* 58(9): 1647–1654 (1987), incorporated herein by reference. This device monitors alkali concentrations in high-temperature, high-pressure process streams by utilizing a nitrous oxide/acetylene flame to excite sodium and potassium in a continuous sample of the process stream. This alkali monitor also utilizes a fiber-optic light transfer system in order to transmit the emitted light to a detaction system by which the data can be analyzed, and alkali concentrations determined. This device is advantageous in that near real-time, short-term information can be provided which can quickly determine damage potential to downstream units, and allow corrective action to be taken when alkali levels exceed component standards.

However, the sensitivity of this real-time alkali monitor is limited by the light collecting means associated with the flame emission. In this prior art device, the monitor used a 1-inch diameter lens to focus the flame emission onto a fiber optic cable. In such a system, only a small portion of the flame is monitored, and flickering of the flame causes substantial noise in the signal which further limits the sensitivity of the detector. The detection limit of the Hensel et al. system has been determined to be roughly 0.75 to about 1.0 part per billion (ppb) for sodium and potassium. It would thus be highly desirable to develop a device which can eliminate the problems with regard to monitoring the flame, increase sensitivity of the flame emission detector, and which can achieve lower detection limits with regard to alkali components in gaseous process streams.

SUMMARY OF THE INVENTION

It has been discovered that a flame emission detection system with enhanced sensitivity can be obtained by employing a device comprising an integrating sphere having an interior coated with a highly diffuse reflective material as the light collection means for the flame light source. Such a device is particularly advantageous in that the sphere collects light from all portions of the flame, not just a localized area which can be imaged with a lens. Secondly, the large collection zone and the multiple diffuse scattering provided by the interior of the sphere integrates the spatial fluctuations of the flame. As a result of these features, localized variations of intensity within the flame are minimized, and the sensitivity of the flame emission detection device employing the sphere will be thus enhanced. The collection efficiency of the integrating sphere is much greater than that provided by a lens, and the device of the present invention can thus be used to provide flame emission detection systems of enchanced resolution and induced noise.

DETAILED DESCRIPTION OF THE PREFERRED EMBODIMENTS

Figure 1:
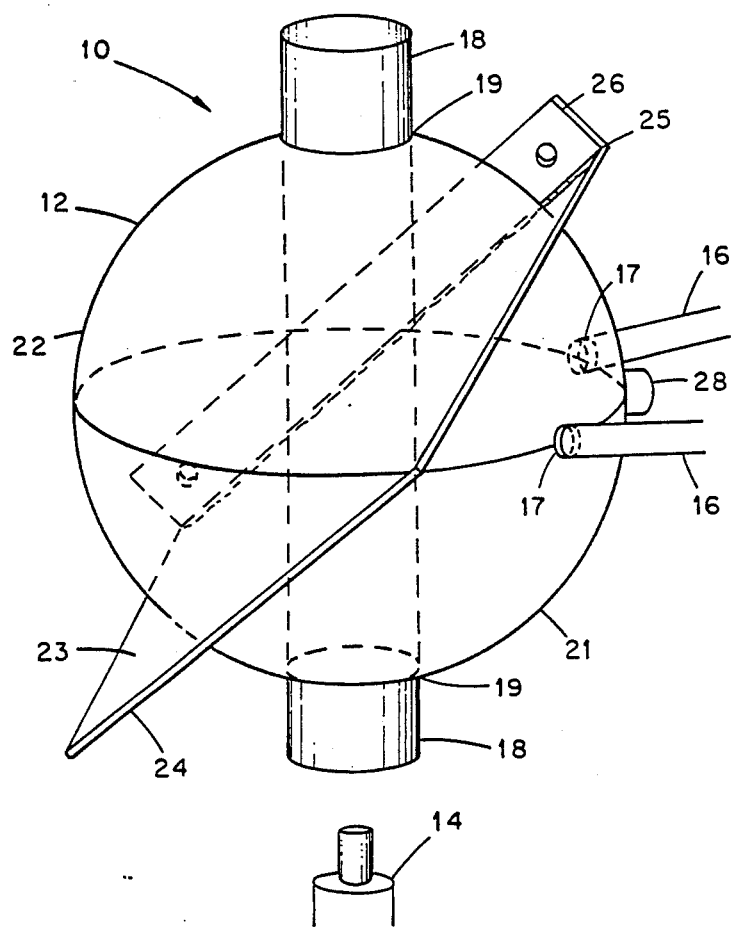
FIG. 1 is a perspective view of the device of the present invention.

A light collection device for enhancing sensitivity and reducing noise in a flame emission detection system in accordance with the present invention is depicted in FIG. 1. The device 10 is comprised of a sphere 12 positionable about a flame, such as provided by burner 14, such that light emitted by the flame is in the interior of the sphere. The device 10 is also provided with a means, such as one or more fiber optic cables 16, for transferring the light produced in the interior of the sphere 12 to a detection device (not shown) wherein the emitted light is analyzed, and levels of particular components of a gas are determined. Preferably, the sphere is provided with openings 17 so that the fiber optic cables 16 can receive the light collected in the interior of the sphere. In the embodiment shown, two openings are provided, and two fiber optic cables are used. However, the number and size of the fiber optic cables used can be varied, as desired. Further, still other known means for receiving and transferring the light from the sphere to the detection means may be employed. Generally, the detection means used with the device of the present invention will comprise photodiode detectors and computer-controlled signal processing means.

The sphere 12 used in the device of the present invention is preferably an "integrating sphere", such as that described in Wolpert, *Electro Optics*, Vol. 15, #8, Aug. 1983 p. 39–40, incorporated herein by reference. The sphere 12 of the present invention has its interior coated with a highly diffuse reflective material at the wavelength of interest so that light entering the interior of the sphere is scattered randomly and thus uniformly distributed within the sphere. The diffuse scattering of light provided in an integrating sphere will be essential in integrating the spatial fluctuations in a flame, and will reduce the effect of localized variations of intensity within the flame. The uniform light collected at the interior of the sphere 12 and transmitted via the fiber optic cables 16 to the detection means provides a much more accurate picture of the flame emission then would a lens which only provides an image of a small volume element of the flame. As a result of the integrating sphere, the resolution or detecting power of a flame emission detection system such as an alkali monitor is significantly enhanced.

In the sphere 12 of the present invention, it is also preferred that a quartz tube 18, or a tube made of materials with similar optical and structural properties, is provided so as to contain the flame when it is projected into the interior of the sphere. The sphere can be provided with holes 19 at its upper and lower ends, and the quartz tube 18 is preferably inserted through holes 19 so as to be centrally located in the interior of the sphere. The device 10 is ideally positioned over burner or flame source 14 such that the flame produced by the burner is contained in quartz tube 18 in the interior of the sphere 12. As a result, the light emitted by the flame is uniformly distributed within the sphere, and a more accurate picture of the components in the combustible gas can be obtained.

The sphere 12 is preferably comprised of two hemispheres, 21 and 22, which are joined at the center at plates 23 and 24. The hemispheres are hinged at joint 25, and the device 10 can be secured by a stationing means, such as plate 26 near joint 25. By constructing the sphere of the present invention in two hemispheres, coating of the interior of the sphere with reflective paint is facilitated, and the sphere can be opened periodically in order to check if the interior coating is intact. The sphere 12 is also preferably provided with port 28 on one side so that cool air can be introduced into the sphere so as to reduce the temperature in the interior of the sphere and prevent overheating. When the device is in operation, it is desirable to have air entrained around the burner between the flame and the walls of the quartz tube, and thus the diameter of tube 18 is preferably about 2-3 times that of the flame. With these features to reduce the chance of overheating, the device of the present invention can be used continuously.

The device of the present invention provides enhanced sensitivity and dampened noise in a flame emission detection system primarily because of two main reasons. First, the sphere collects light from all portions of the flame which can be contained within the sphere, not just a localized area which would be imaged with a lens. Therefore, species which emit from localized zones of temperature within the flame because of their particular physical properties will still be within the sensitive collection zone of the sphere which is much greater than in previous models. Second, the large collection zone and the multiple diffuse scattering will integrate the spatial fluctuations of the flame. This reduces the effect of localized variations of intensity within the flame because the sphere provides a large zone with a uniform light collection efficiency. The fiber optic bundle attached to the side of the sphere will "see" the diffuse reflecting surface of the sphere rather than the image of a small volume element of the flame. The light collecting efficiency of the integrating sphere is a function of the size of the sphere, the number and size of openings in the sphere, and the reflectivity of the interior surface of the sphere. With proper selection of these variables, the collection efficiency of the integrating sphere for a large light emitting volume is much greater than for a lens.

A device in accordance with the present invention has been constructed and used with the on-line, real-time alkali (sodium and potassium) monitor developed by Hensel et al. The device of the present invention uses a 10 inch diameter integrating sphere (Lab Sphere, North Sutton, New Hampshire) having upper and lower 53 mm diameter holes, two 0.5 inch openings on the circumference at the center of the sphere, through which fiber optic cables are placed, and a one inch port on the side of the sphere, which acts as the cooling air inlet. As indicated above, however, these dimensions can be varied as desired depending on the application, e.g., flame dimension, optical fiber size, cooling air requirements.

The interior of the sphere is coated with a diffuse reflectance paint, such as Eastman Kodak white reflectance paint, which has a reflectivity in excess of 99 percent over the visible spectrum and randomly scatters light hitting the sphere's interior walls. As a result of the coating, the light entering the interior is uniformly distributed within the sphere. A quartz tube (51 mm outside diameter, 47 mm inside diameter) of 61 cm in length is inserted in the sphere, and the nitrous oxide/acetylen flame burner of the alkali monitor is positioned below the quartz tube such that the flame will be contained in the tube. The alkali monitor burner produces a flame which is approximately 50 cm tall, and this should be sufficient to ensure that the flame extends through the length of the sphere. The tube's diameter in this case is roughly about 2-3 times the general diameter of the flame so as to reduce the chance of overheating and softening the quartz tube. Further, air is entrained around the burner between the flame and the tube, and approximately 10 liters per minute of cooling air is injected into the sphere through the air inlet port on the sphere wall. This sphere has been operated continuously for up to 8 hours without overheating.

Figure 2:
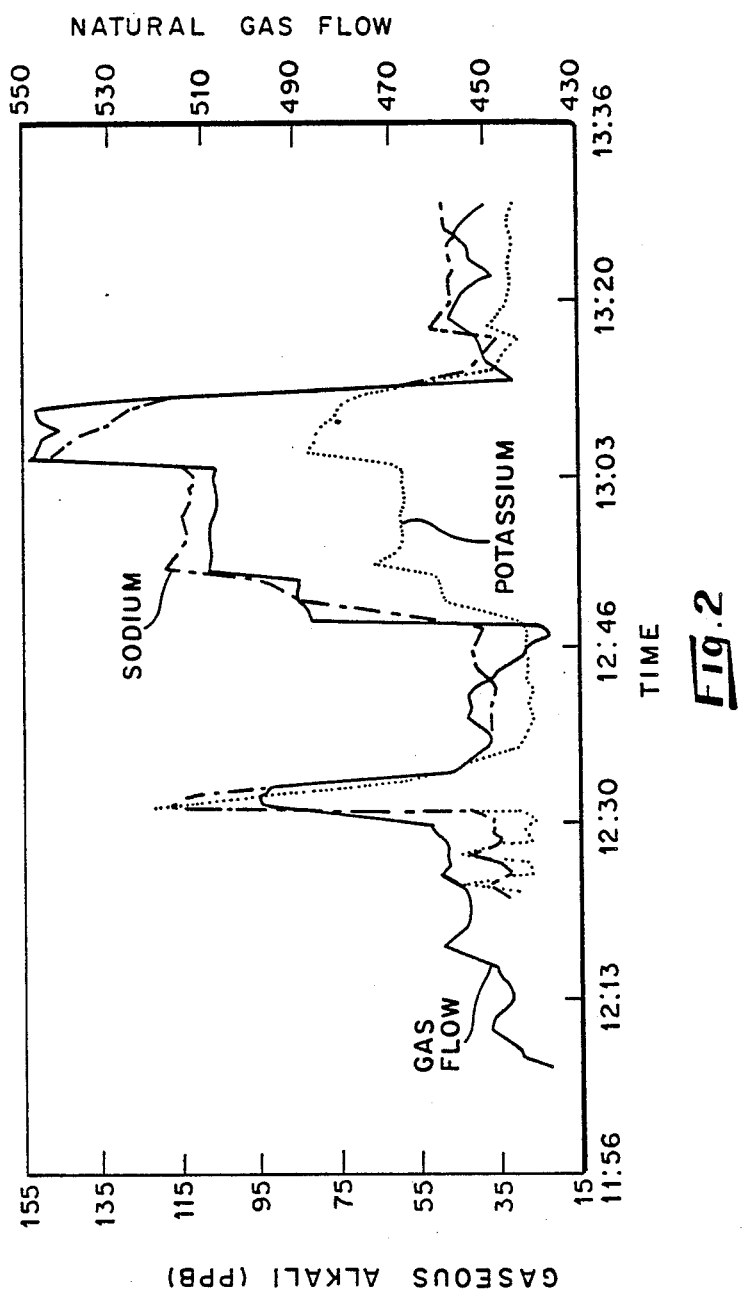
FIG. 2 is a graphic representation of gaseous alkali concentrations in exhaust from natural gas combustion as measured by a flame emission detector utilizing the device of the present invention.

The alkali monitor employing the light collection device of the present invention has been able to achieve much greater levels of sodium and potassium detection that what was obtained in the prior art monitor which employed a lens as the light collecting means. The device of the present invention when used in the alkali monitor provided a detection limit of 410 parts per trillion (ppt) for sodium and 350 ppt for potassium, as compared with the 0.75 to 1.0 parts per billion detection limit associated with the previous monitor. Use of the light collection device described above thus results in a substantial improvement over the prior art design. Use of the present invention in the real-time monitoring of alkali concentrations in the exhaust of a coal/water mixture-fired combustor has been carried out, and the concentrations of sodium and potassium recorded are represented graphically in FIG. 2.

The integrated sphere light-collecting device of the present invention has been used successfully with a flame emission source, and has been shown to provide significant improvements over the lens collection system previously employed in an alkali monitor using a nitrous oxide/acetylene flame. The device of the invention can also be adapted to other similar flame emission detection systems, such as a flame atomic emission spectrometer, an inductively coupled plasma spectrometer, or any technique where the light emission is spatially dependent on some source property which may vary over time. In real-time alkali monitors and these other systems, the present invention can be utilized to enhance sensitivity, reduce noise, and provide a greater level of detection for the elements being assessed.

Although the present invention has been described relative to exemplary embodiments thereof, it will be understood by those skilled in the art that variations and modifications can be effected in these exemplary embodiments without departing from the scope and spirit of the invention.

What is claimed is:

1. A light collection device for enhancing sensitivity and reducing noise in a flame emission detection system comprising:

a hollow sphere having interior walls coated with a highly diffuse reflective material and having openings through the interior walls at upper and lower ends of the sphere with said openings being of a diameter less than about three times the diameter of a flame provided in the interior of the sphere;

burner means in registry with the lower opening in the sphere for providing a vertically extending flame in the interior of the sphere intermediate said openings so that light emitted by the flame is uniformly reflected from the coated walls by diffuse scattering within the sphere;

an elongated transparent tube means extending through the interior of said sphere and said upper and lower openings and disposed about said flame and for uniformly distributing the light emitted by the flame throughout the interior of the sphere; and light receiving means in registry with the interior of the sphere for transferring light indicative of essentially all portions of the vertical flame from within the sphere to a detection means.

2. A light collection device according to claim 1, wherein passageway means are in registry with the interior of the sphere on one side thereof intermediate the upper and lower openings for introducing air into the sphere about the transparent tube means.

3. A light collection device according to claim 1, wherein the openings through the transparent tube means are of a diameter in the range of about 2 to 3 times as great as the diameter of the vertically extending flame.

4. A light collection device according to claim 1, wherein the transparent tube means is a quartz tube.

* * * * *